United States Patent
Shimoda et al.

(10) Patent No.: US 6,721,047 B2
(45) Date of Patent: Apr. 13, 2004

(54) METHOD AND APPARATUS FOR INSPECTING DEFECTS OF A SPECIMEN

(75) Inventors: Atsushi Shimoda, Hiratsuka (JP); Sachio Uto, Yokohama (JP); Minoru Yoshida, Yokohama (JP); Shunji Maeda, Yokohama (JP); Toshihiko Nakata, Hiratsuka (JP)

(73) Assignee: Hitachi, Ltd. (JP)

( * ) Notice: Subject to any disclaimer, the term of this patent is extended or adjusted under 35 U.S.C. 154(b) by 98 days.

(21) Appl. No.: 09/944,858

(22) Filed: Aug. 31, 2001

(65) Prior Publication Data

US 2002/0036769 A1 Mar. 28, 2002

(30) Foreign Application Priority Data

Sep. 18, 2000 (JP) ........................................ 2000-282144

(51) Int. Cl.[7] .......................... G01N 21/00; G01N 21/88
(52) U.S. Cl. .................................. 356/237.5; 250/559.45
(58) Field of Search ........................... 356/237.1, 237.2, 356/237.3, 237.4, 237.5; 250/559.45, 559.46, 201.4

(56) References Cited

U.S. PATENT DOCUMENTS 5,098,191 A * 3/1992 Noguchi et al. ............. 356/394
6,091,075 A * 7/2000 Shibata et al. .......... 250/559.44
6,400,454 B1 * 6/2002 Noguchi et al. .......... 356/237.3
6,492,649 B1 * 12/2002 Nei et al. .................... 250/548

FOREIGN PATENT DOCUMENTS

JP 4-368146 * 12/1992
JP 06-265773 9/1994

* cited by examiner

Primary Examiner—Alan Mathews
(74) Attorney, Agent, or Firm—Townsend and Townsend and Crew LLP

(57) ABSTRACT

The object of the invention is to provide high-sensitivity detection of fine patterns on a transparent inter-layer insulative film and defects on the same layer. Detection is performed with lower-layer patterns and defects on the same layer defocused, thus allowing detection of just the defects from the process that is intended for inspection. An inspection apparatus for a specimen on which a plurality of patterns intended to have identical shapes are arranged in a uniform manner includes: an imaging optical system with a relationship between illumination wavelength and objective lens numerical aperture that provides a resolution of no more than 0.18 microns, or preferably no more than 0.13 microns; an opto-electric converter disposed at an imaging position of the imaging optical system; an auto-focus optical system formed with an optical path disposed separate from the imaging optical system, with illumination applied at an incident angle of at least 85 degrees, preferably at least 88 degrees; means for adjusting a focal position of the imaging optical system based on a detection signal from the auto-focus optical system; and means for processing electronic signals from the opto-electrical converter.

17 Claims, 15 Drawing Sheets

(a)

(b)

(a)

(b)

(a)

(b)

(a)

(b)

METHOD AND APPARATUS FOR INSPECTING DEFECTS OF A SPECIMEN

BACKGROUND OF THE INVENTION

The present invention relates to a method and apparatus for inspecting defects of a specimen. More specifically, the present invention relates to a method and apparatus for inspecting defects of a specimen that is suitable for use in detecting optical images of fine patterns formed on transparent films of a semiconductor wafer.

Optical defect inspection apparatuses are equipped with microscope systems with high-precision auto-focus functions to provide optical imaging of fine patterns. This type of technology for microscope systems is presented in Japanese laid-open patent publication number Hei 6-265773 ("Autofocus apparatus for microscopes"). The conventional technology described in this publication uses a TTL (Through The Lens) system where an auto-focus beam passes through the objective lens.

In TTL systems, both the imaging beam and the auto-focus beam pass through the objective lens. As a result, a high correlation between auto-focus detection results and imaging contrast is provided even when there is variation in the focal distance due to slight environmental changes such as temperature changes. Thus, TTL systems are standard in auto-focus systems used in microscope systems for detecting fine patterns formed on semiconductor wafers.

Currently, 0.18 micron widths are dominant as the pattern rule for semiconductor devices. This is expected to shift to 0.13 micron widths in the future. To form such fine circuit patterns, CMP (Chemical Mechanical Polishing) becomes necessary.

FIG. 4 shows cross-section drawings of a CMP-processed wafer. FIG. 4(a) shows a wafer with a lower-layer circuit pattern 1 formed. FIG. 4(b) shows an inter-layer insulative film 2, a transparent layer, formed on the lower-layer circuit pattern 1. The inter-layer insulative film 2 forms a mount where the lower-layer circuit pattern 1 is formed, resulting in unevenness in the inter-layer insulative film surface. This unevenness must be flattened out in order to allow a fine pattern to be formed on the inter-layer insulative film 2. This is because the exposure apparatus used to form the fine patterns has a shallow depth of focus, which prevents the unevenness from being ignored.

The flattening of this unevenness is performed with CMP processing. More specifically, a polishing pad is pressed against the surface of the inter-layer insulative film (transparent film) 2 and the surface is polished while a chemical abrasive (slurry) is applied. This provides a flat surface 3 as shown in FIG. 4(c).

A fine circuit pattern 4 can be formed on this flat surface 3, as shown in FIG. 4(d). With current and future semiconductor products with pattern widths of 0.18–0.13 microns, fine circuit patterns will be formed on CMP-processed transparent film. For this reason, defect inspection apparatuses need to provide optical features that allow precise detection of these circuit patterns.

However, an issue comes up regarding the auto-focal position in TTL systems for CMP-processed transparent films. This will be described with references to FIG. 5 and FIG. 6. FIG. 5(a) shows the angle of divergence θ of an objective lens 5. The divergence angle θ and the numerical aperture NA have the following relationship:

$$NA = \sin\theta \quad \text{Equation (1)}$$

FIG. 5(b) illustrates the relationship indicated in Equation (1). As FIG. 5(b) shows, the divergence angle θ is about 72 degrees even at NA=0.95, the setting closest to the NA that would be used under atmospheric pressure.

FIG. 6 shows the relationship between the angle of incidence i of a beam entering a transparent film and the reflectance R. Black circles indicate S-polarized light and black squares indicate P-polarized light. Reflectance R is a function of the angle of incidence i and changes depending on the polarization state. As the figure shows, even with the better S-polarized light, at 72 degrees (value 6 in the figure), there is only approximately 30% reflectance (value 7 in the figure), with the remaining 70% being transmitted into the transparent film. Thus, almost all of a TTL auto-focus beam will be transmitted into the transparent film and reflected from the lower-layer pattern before it is detected.

FIG. 7 shows a beam 8 illuminated from a TTL system passing through the transparent inter-layer insulative film 2 and focused on a surface 10 of a lower-layer circuit pattern 1. As a result, the object of detection, i.e., the fine pattern 4 on the transparent insulative film 2 and defects 11 formed on this layer, are defocused while the focus is on items not intended for detection, i.e., the lower-layer circuit pattern 1 formed below the transparent inter-layer insulative film 2 and defects 12 formed on this layer.

In semiconductor device defect inspections, identifying the layer at which a detected defect is present is important. Only by detecting defects by layer can prevention measures be taken to reduce defects. However, as shown in FIG. 7, if the detection beam is focused on a position other than the intended position, the accuracy of defect detection for that position is decreased drastically.

SUMMARY OF THE INVENTION

The present invention provides a defect inspection method and apparatus that is capable of detecting defects by using images captured at high resolutions with precise focus on the surface of a transparent film. This allows defects formed on fine patterns on the thin film to be detected in a highly sensitive manner.

The present invention also provides stable output unaffected by environmental temperature changes of images captured at high resolutions with precise focus on the surface of a transparent film.

The present invention is equipped with the technical means described below.

An inspection apparatus for a specimen on which a plurality of patterns intended to have identical shapes are arranged in a uniform manner includes: an imaging optical system with a relationship between illumination wavelength and objective lens numerical aperture that provides a resolution of no more than 0.18 microns, or preferably no more than 0.13 microns; an opto-electric converter disposed at an imaging position of the imaging optical system; an auto-focus optical system formed with an optical path disposed separate from the imaging optical system, with illumination applied at an incident angle of at least 85 degrees, preferably at least 88 degrees; means for adjusting a focal position of the imaging optical system based on a detection signal from the auto-focus optical system; and means for processing electronic signals from the opto-electrical converter.

According to another aspect of the present invention, the defect inspection apparatus also includes: means for detecting temperature; means for storing a relationship between temperature and focal position offset measured ahead of time or calculated through simulations; means for predicting a focal position offset using the relationship between temperature and focal position offset and based on temperature detection results from temperature detecting means; and means for correcting focal position offsets based on the prediction from this means.

Another aspect of the present invention, a defect inspection apparatus includes: a focal position measurement optical system formed by splitting an imaging optical system; a specimen, separate from the item on which detection is to be performed, serving as an object of measurement by the focal position measurement optical system; and means for measuring a focal position offset on the specimen using the focal position measurement optical system and adjusting an offset for the auto-focus optical system disposed separate from the imaging optical system based on these measurement results.

These and other objects, features and advantages of the invention will be apparent from the following more particular description of preferred embodiments of the invention, as illustrated in the accompanying drawings.

DESCRIPTION OF THE PREFERRED EMBODIMENTS

Figure 1:
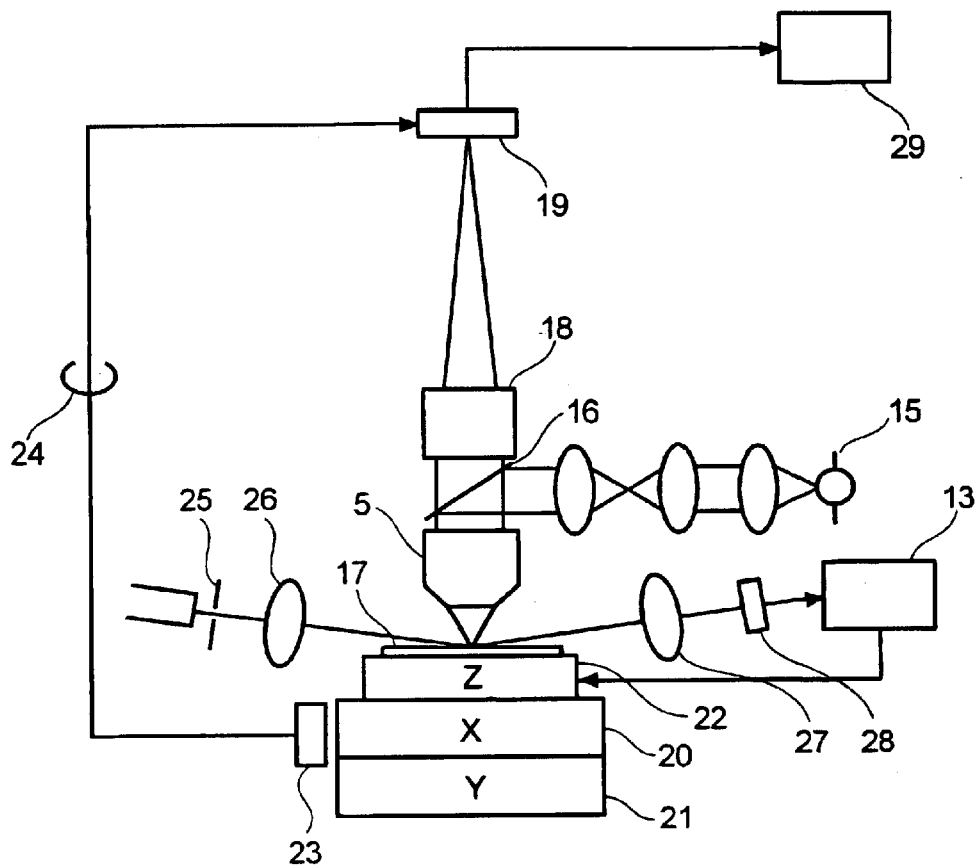
FIG. 1 is a drawing for the purpose of describing the architecture of a semiconductor wafer defect inspection apparatus according to a first embodiment of the present invention.

The following is a description of the embodiments of the present invention, with references to the drawings. FIG. 1 shows the architecture of a defect inspection apparatus for semiconductor wafers according to a first embodiment of the present invention.

In the architecture shown in FIG. 1, a beam from an illuminating light source 15 is reflected by a half mirror 16. The beam passes through an objective lens 5 and illuminates the specimen, a wafer 17, at an angle. The reflected beam from the wafer 17 passes through the half mirror 16 and an image is formed on an image sensor 19 by an imaging lens 18. The wafer 17 is secured on X, Y, Z stages (20, 21, 22).

The signal from the image sensor 19 is read based on a timing signal 24 generated by a linear scale 23 added to the X stage 20 each time the X stage is moved a fixed amount.

In the auto-focus optical system, an illumination beam passing through a slit 25 is focused on the surface of the wafer 17 by an imaging lens 26, and a slit image is projected. The beam reflected from the surface of the wafer 17 forms an image on a light-receiving sensor 28 via an imaging lens 27.

Figure 2:
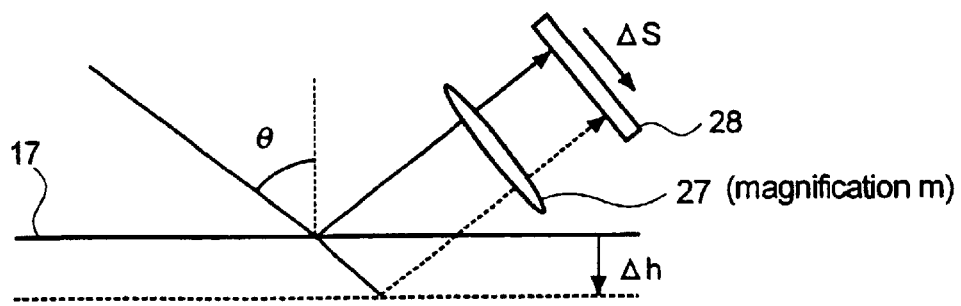
FIG. 2 is a drawing for the purpose of illustrating the detection principles of an auto-focus optical system used in the embodiments of the present invention.

FIG. 2 illustrates the principles involved in the auto-focus optical system. The displacement $\Delta S$ over the light-receiving sensor 28 is expressed as follows:

$$\Delta S = 2m \times \Delta h \times \sin\theta \qquad \text{Equation (2)}$$

where $\theta$ is the incident angle of the illumination beam of the auto-focus optical system, $\Delta h$ is the height displacement of the wafer 17, and m is the magnification of the imaging lens 27.

If the light-receiving sensor 28 is a two-piece diode, the offset is adjusted so that the two diodes receive equal light at the focal position of the imaging optical system. Since the light-receiving position over the sensor is displaced by $\Delta S$ when the wafer height is displaced by $\Delta h$, there will be an imbalance between the light received by the two diodes. In order to have the wafer 17 positioned where there is balanced light, the Z stage 22 is controlled by a Z stage controller 13 so that the wafer height is continuously adjusted for the focal position of the imaging optical system.

Figure 3:
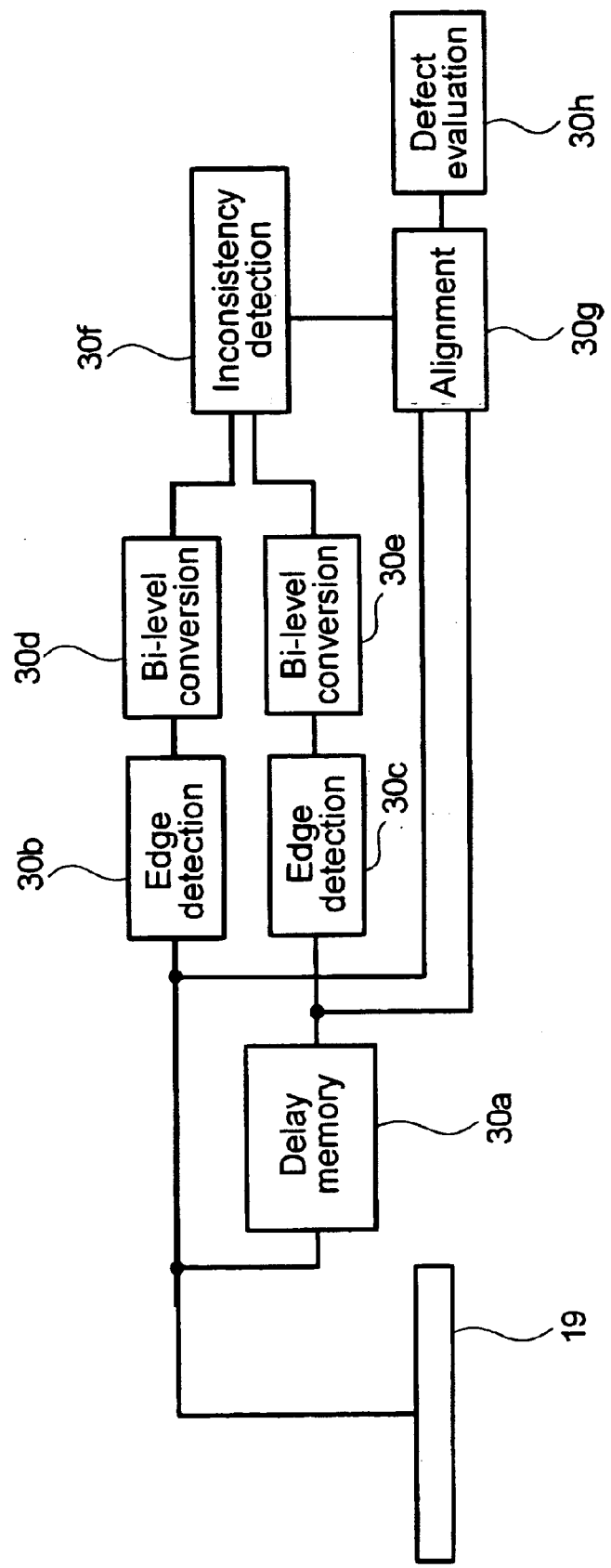
FIG. 3 is a block diagram showing the architecture of an image processing module from FIG. 1.

FIG. 3 shows the architecture of an image processing module 29, which processes the output from the image sensor 19. A delay memory 30a delays the output from the image sensor 19 by a time interval corresponding to the displacement of the wafer 17 by one chip along the X axis. Thus, the output signal from the image sensor 19 and the output signal from the delay memory 30a will correspond to image signals for adjacent chips. The image signal from the image sensor 19 and the image signal from the delay memory 30a are sent to edge detection circuits 30b, 30c, which detect pattern edges in the specimen patterns. Bi-level conversion circuits 30d, 30e perform bi-level conversion of the detected pattern edges. Next, an inconsistency detection circuit 30f shifts the pattern edges output from the edge detection circuit 30b and the pattern edges output from the edge detection circuit 30c in order to determine offset values that minimize disparities between the signals. Then, an alignment circuit 30g uses the image signal from the image sensor 19 and the image signal from the delay memory 30a, shifts the inconsistent image elements by the determined offset, and outputs the results to a defect evaluation circuit 30h.

The defect data detected by the image processing module 29 is sent to an input/output module via a controller. The controller is a conventional computer system that provides overall control over the defect inspection apparatus and overseas communication with external systems. The input/output module is a conventional computer system that performs functions such as displaying inspection information and overseeing the interface that receives instructions from the operator. Regarding its relationship with the auto-focus system, an auto-focus offset entered by the operator into the input/output module is transferred to the controller, and the controller sends instructions to the Z stage controller 13. Also, the auto-focus offset is recorded as an inspection conditions file and transferred by the controller via a conventionally known network to be saved in an external database. The operations of the auto-focus offset will be described later.

Figure 4:
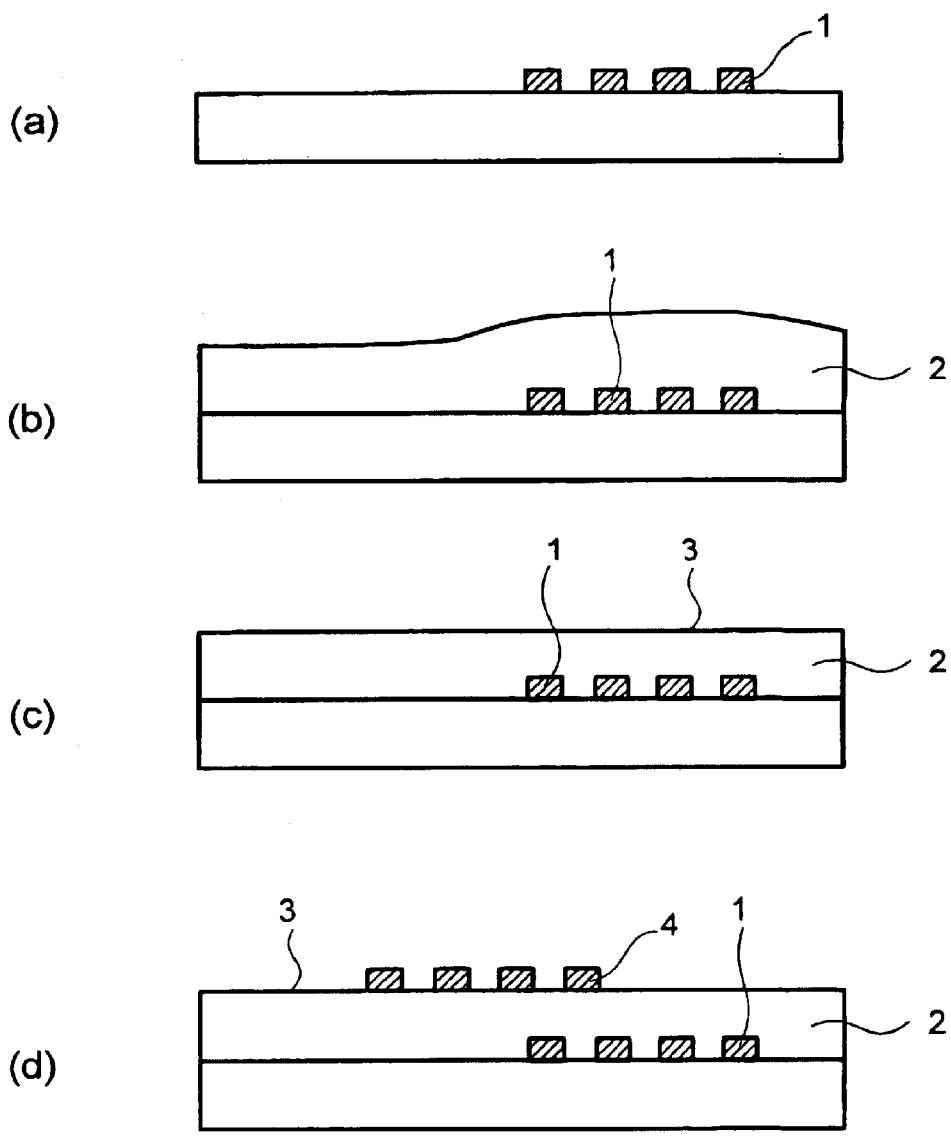
FIG. 4 shows cross-section drawings of a wafer on which CMP processing is applied.
Figure 5:
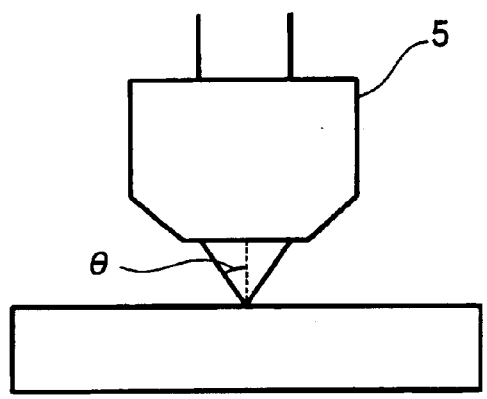
FIG. 5 is a drawing for the purpose of illustrating the relationship between the numerical aperture of an objective lens and divergence angles.
Figure 5:
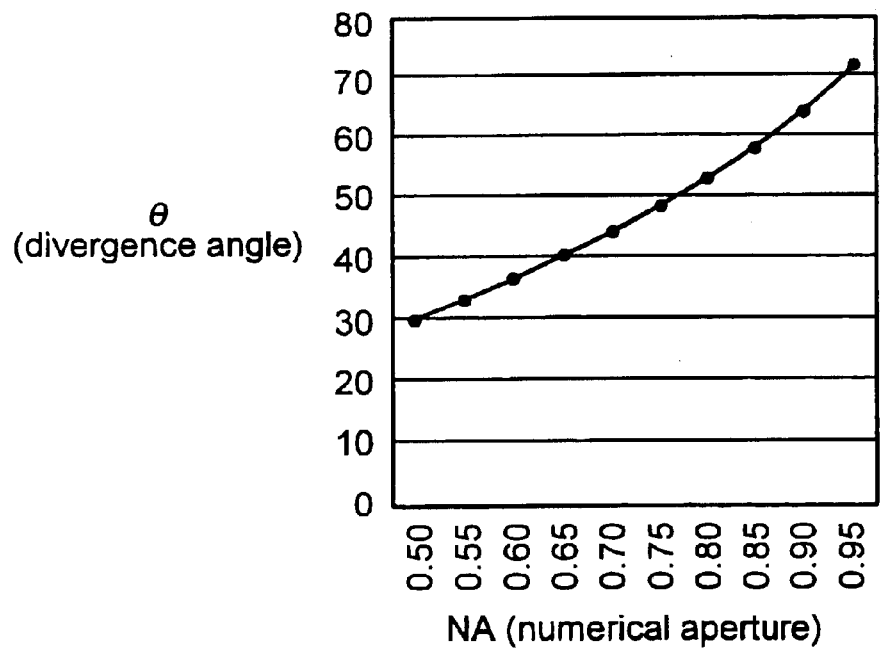
Figure 6:
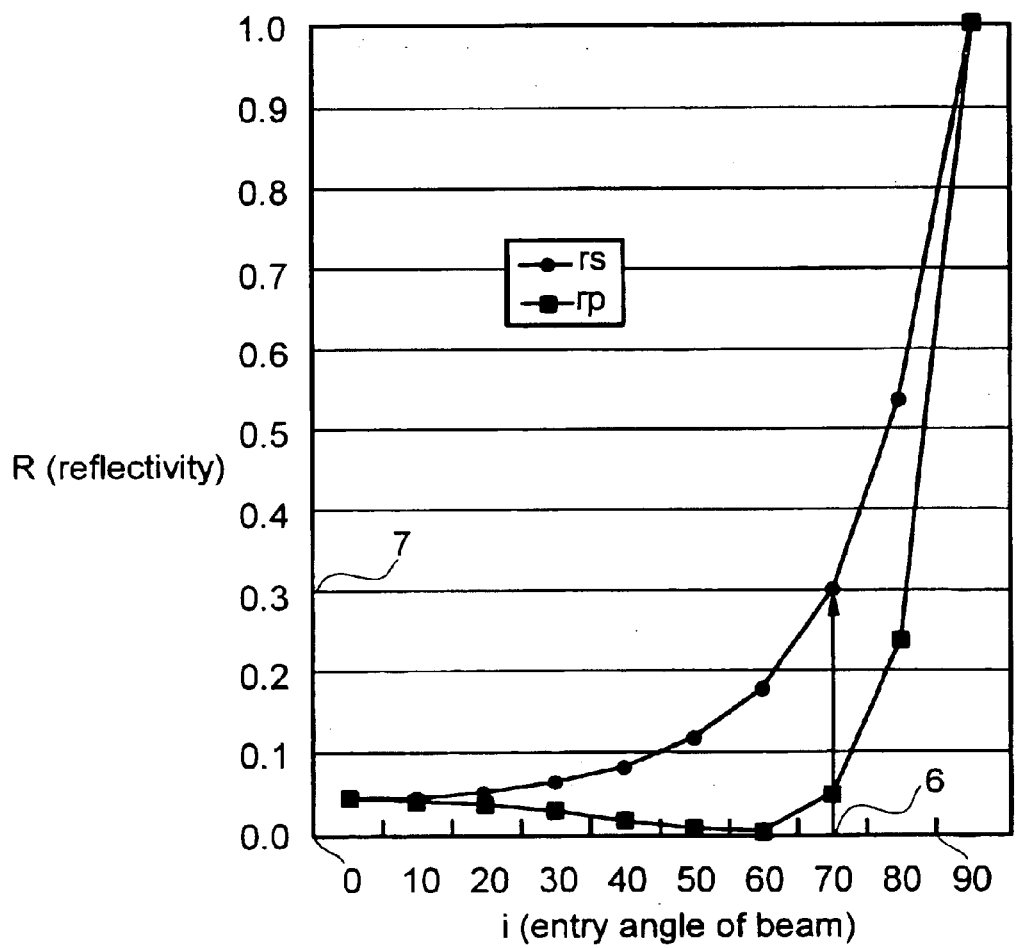
FIG. 6 is a drawing for the purpose of illustrating the relation between the incidence angle and reflectivity of a beam projected onto a transparent film.
Figure 7:
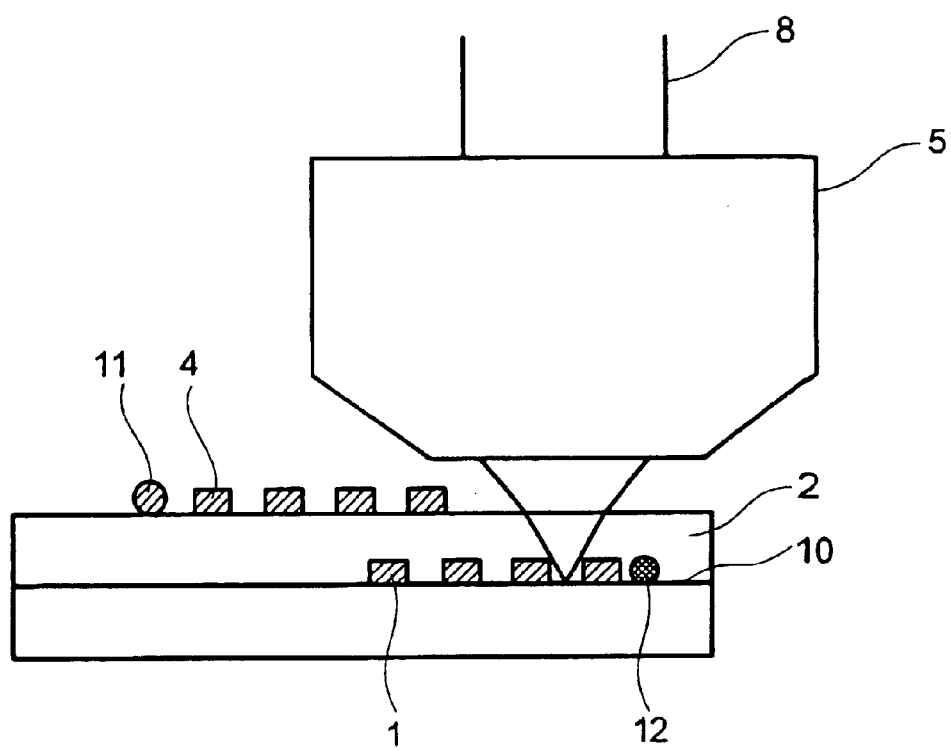
FIG. 7 is a drawing for the purpose of illustrating how a TTL auto-focus optical system focuses on a lower-layer pattern.

The circuit rule of the semiconductor device, i.e., the specimen, has been decreasing at a rate of 1/sqrt(2) every three years, with the current minimum pattern width of 0.18 microns expected to be reduced to 0.13 microns in the future. To form these fine circuit patterns, CMP processing as described above with reference to FIG. 4 becomes necessary, and detection of fine patterns forms on transparent inter-layer insulative films that have been CMP processed becomes necessary.

The following is a description of conditions needed for stable detection of a fine pattern 4 formed on a CMP-processed, transparent inter-layer insulative film 2.

In general, the resolution Res of a microscope optical system can be expressed as:

$$Res = 0.5 \times \lambda / NA \qquad \text{Equation (3)}$$

where $\lambda$ is the wavelength of the illumination beam and NA is the numerical aperture of the objective lens.

FIG. 8(a) provides a schematic illustration of the definitions used in Equation (3). Assuming a repeating pattern 31 of lines and spaces, Equation (3) indicates the conditions for separately detecting adjacent pattern images 33 at a focal position 32 of the optical system.

FIG. 8(b) shows the relationship between the numerical aperture NA of the objective lens, the wavelength $\lambda$ of the illumination beam, and the resolution Res.

As Equation (3) and FIG. 8(b) show, increasing the resolution (decreasing the value of Res) requires either decreasing the illumination wavelength $\lambda$ or increasing the numerical aperture NA of the objective lens. There are physical restrictions on both of these factors, however, and these restrictions determine the actual possible range. With regard to the illumination wavelength $\lambda$, the lower limit is determined by the conversion efficiency of the opto-electric converter (the image sensor 19). In opto-electric conversion, the electrons generated when a photo impacts the sensor is referred to as the quantum yield, and this quantum yield is a function of the beam wavelength. With existing opto-electrical converters, the lower limit of the illumination wavelength $\lambda$ obtainable with actual quantum yields is approximately 0.2–0.3 microns (indicated by a range 34 in FIG. 8(b)).

Examples of microscope illumination light sources falling in this $\lambda=0.2–0.3$ micron range include xenon lamps and mercury xenon lamps, which provide continuous wavelength illumination. Also, it is known that by combining a non-linear optical element with a YAG laser ($\lambda=0.532$ micron), for example, can provide a 0.266 micron wavelength (the second harmonic). From FIG. 8(b), it can be seen that with an illumination wavelength range of 0.2–0.3 microns, a resolution Res=0.15 microns roughly equivalent to circuit pattern widths (value 35 in FIG. 8(b)), the NA would be approximately in the range of 0.7–0.9 (value 36 in FIG. 8(b)).

The depth of focus DOF can be obtained from the illumination wavelength $\lambda$ and the numerical aperture NA using the following equation:

$$DOF = 0.5 \times \lambda / (NA^2) \qquad \text{Expression (4)}$$

FIG. 9(a) provides a schematic illustration of the definitions used in Equation (4). The figure indicates that good focus characteristics can be maintained within a +/−DOF range 38 relative to a best focal position 37 of the imaging optical system.

FIG. 9(b) shows the relationship between the numerical aperture NA of the objective lens, the illumination wavelength $\lambda$, and the depth of focus DOF. To provide a resolution of 0.15 microns (roughly equal to the circuit pattern width), the depth of focus would be approximately +/−0.2 microns with the NA 36 (FIG. 9(b)) and the illumination wavelength $\lambda$34 (FIG. 9(b)). Thus, circuit pattern defects within this range can be analyzed with good resolution while moving away from this range will result in decreasing contrast and de-focused images. As a result, the height detection error of the auto-focus optical system must be less than the depth of focus value described above.

Figure 10:
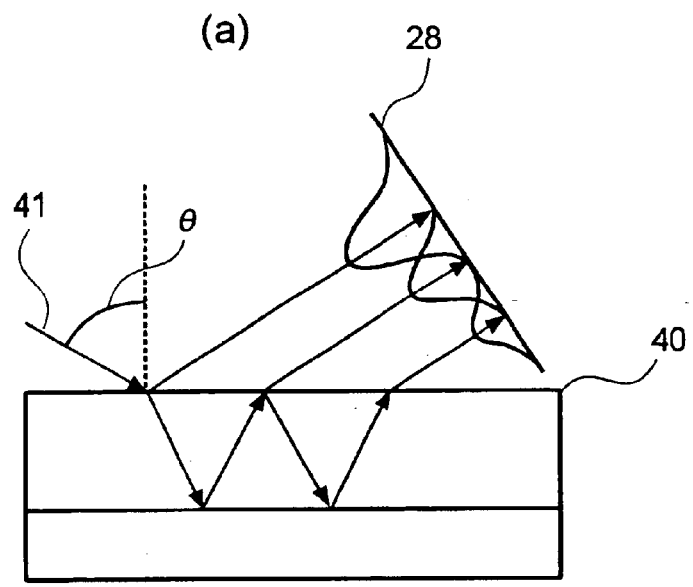
FIG. 10 is a drawing for the purpose of illustrating the relation between the illumination angle and height detection error in an auto-focus optical system for a thin film.
Figure 10:
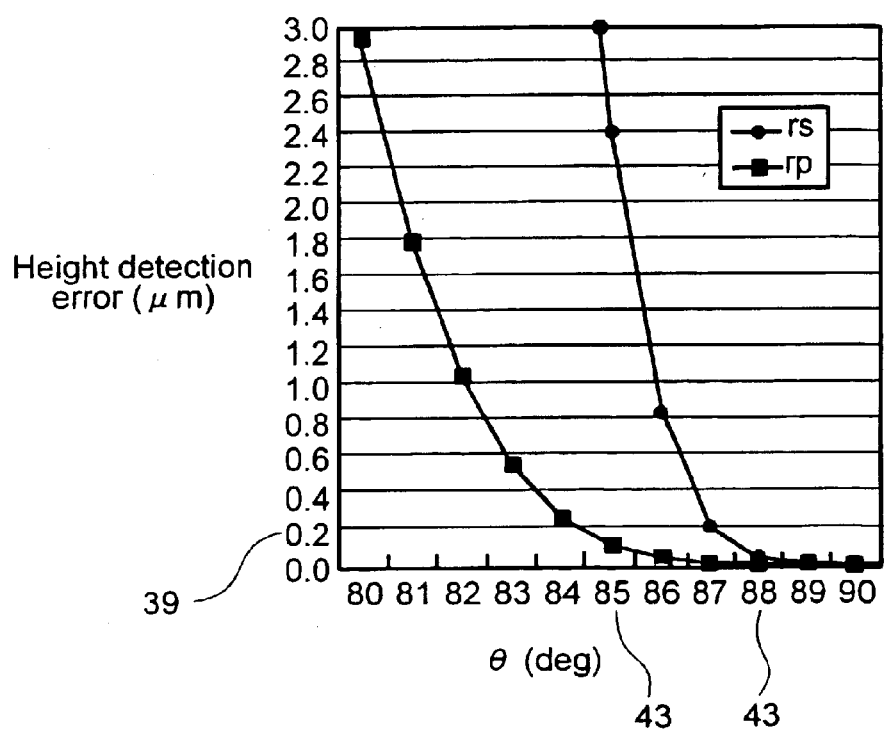

FIG. 10 shows the relationship between the illumination angle $\theta$ of the auto-focus optical system and height detection error with regard to a transparent film 40. When a beam 41 enters the transparent film 40 at the illumination angle $\theta$, $$Rp = (\cos i_1/n_1 - \cos i_2/n_2)/(\cos i_1/n_1 + \cos i_2/n_2) \qquad \text{Equation (5)}$$

$$Tp = 1 - Rp \qquad \text{Equation (6)}$$

$$Rs = (n_1 \times \cos i_1 - n_2 \times \cos i_2)/(n_1 \times \cos i_1 + n_2 \times \cos i_2) \qquad \text{Equation (7)}$$

$$Ts = 1 - Rs \qquad \text{Equation (8)}$$

Based on polarization, the beam 41 will divide into a reflection beam and a transmission beam according to Equation (5) through Equation (8). R is the amplitude reflection rate, T is the amplitude transmission rate, s and p indicate polarization, 1 and 2 indicate mediums, n is the refraction index, and i is the incident angle.

FIG. 10(b) shows the relationship between the illumination angle $\theta$ and the height detection error when: air has a refraction index of 1, the transparent film has a refraction rate of 1.5, the transparent film has a thickness of 1 micron, and the lower film layer has a reflectivity of 1 (height detection error is assumed to be maximum). In the figure, black circles indicate P-polarized light and black squares indicate S-polarized light.

FIG. 10(b) shows that for random polarization (assuming P-polarization as the worst-case), which has low light loss for the illumination beam, the angle $\theta$ must be 88 degrees (value 43 in FIG. 10(b)) for the height detection error to be less than the focal depth +/−0.2 microns (value 39 in FIG. 10(b)). Taking light loss into account, an angle of 85 degrees or higher (value 42 in FIG. 10(b)) can be used for S-polarized light. These illumination angles are difficult to implement for TTL systems.

Figure 8:
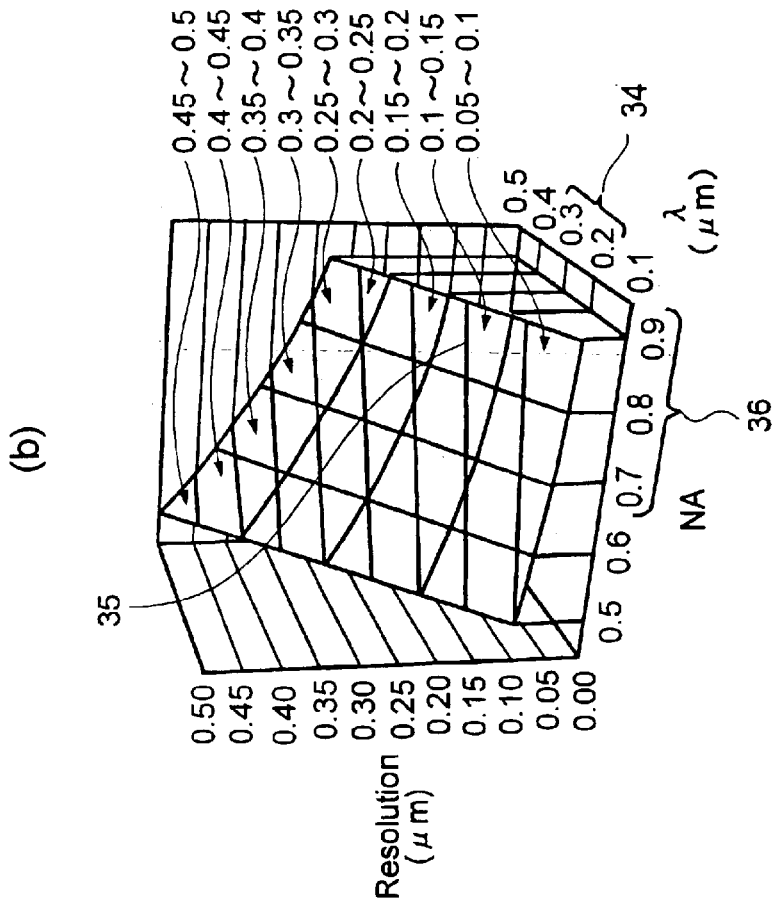
FIG. 8 is a drawing for the purpose of illustrating the relation between NA, $\lambda$, and resolution.
Figure 8:
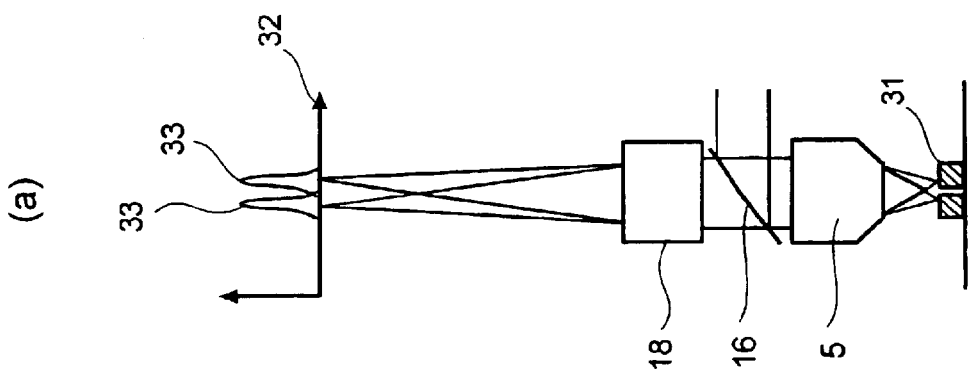
Figure 9:
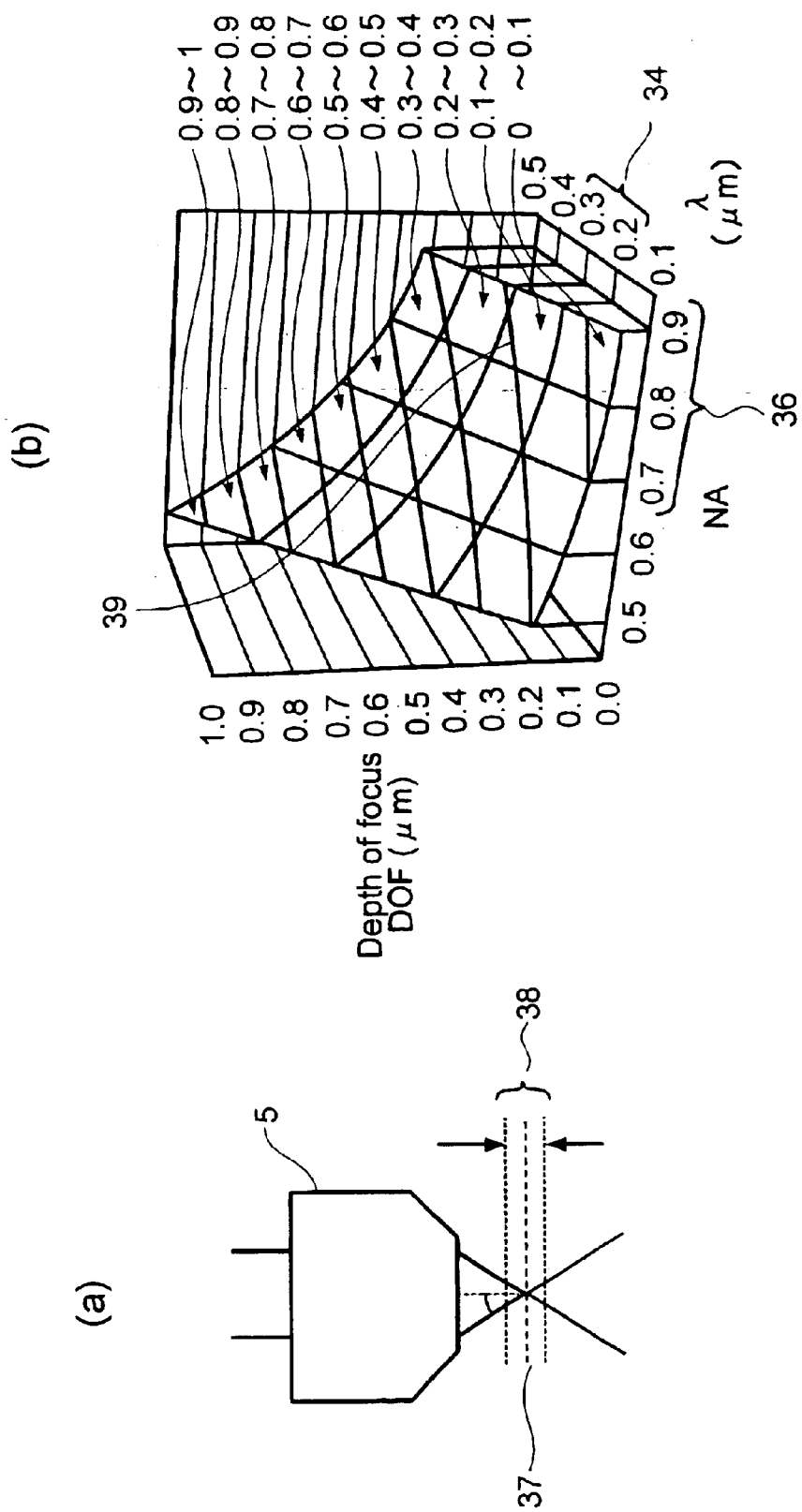
FIG. 9 is a drawing for the purpose of illustrating the relation between NA, $\lambda$, and depth of focus.
Figure 11:
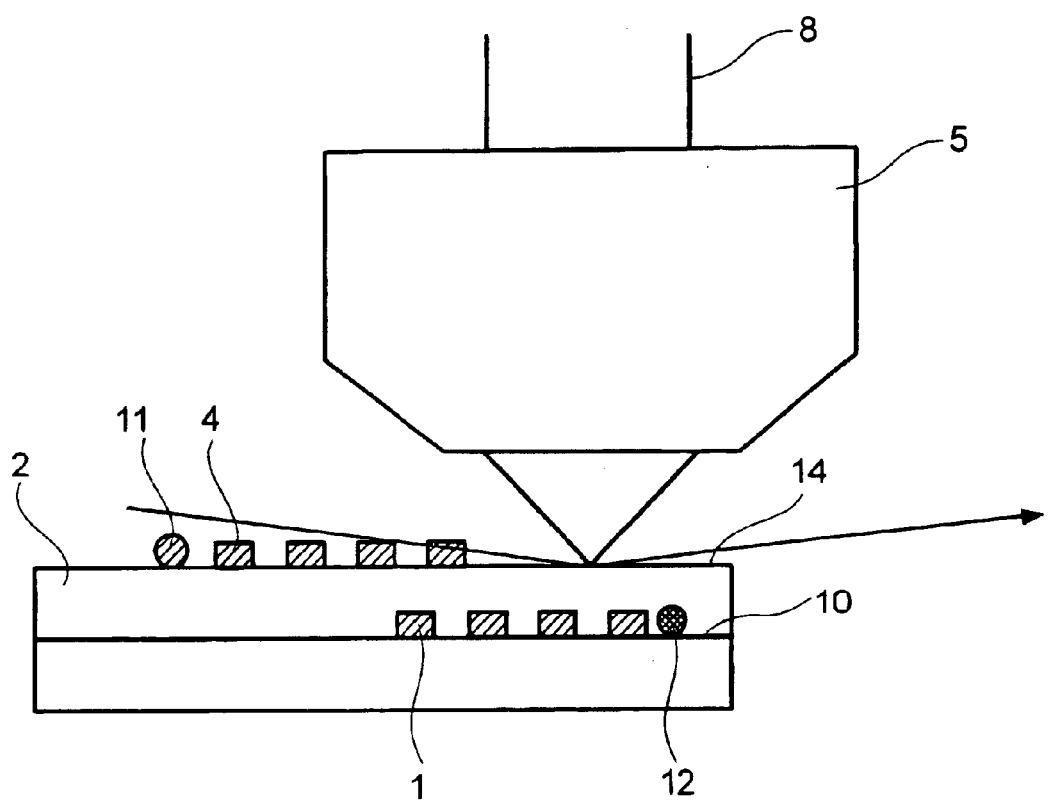
FIG. 11 is a drawing for the purpose of illustrating how a fine pattern on a thin film is imaged in a first embodiment of the present invention.

FIG. 11 shows a defect inspection apparatus that implements the conditions illustrated in FIG. 8 through FIG. 10.

The figure shows a fine pattern on a transparent film being imaged. Assuming an illumination wavelength λ=0.266 microns and a numerical aperture NA=0.85 for the objective lens, the resolution Res and the depth of focus DOF in the imaging optical system would be:

$$Res = 0.5 \times 0.266/0.85 = 0.156 \text{ microns}$$

$$DOF = 0.5 \times 0.266/(0.85 \times 0.85) = 0.184 \text{ microns}$$

Furthermore, by using S-polarized light with an incident angle of at least 85 degrees as the auto-focus illumination beam, the height detection error can be kept to less than +/− 0.2 microns. As a result, the image detected by the defect inspection apparatus can be focused on a surface 14 of a transparent film (transparent inter-layer insulative film) 2, allowing good imaging of the fine circuit pattern 4 (with a pattern width of 0.15 microns) formed on the transparent film 2. This provides high-sensitivity detection of the defect 11 on this layer. If the film thickness of the transparent film 2 is 0.2 microns, the contrast for the lower-layer circuit pattern 1 decreases, thus preventing the detection of a defect 12, which should not be detected anyway.

Figure 12:
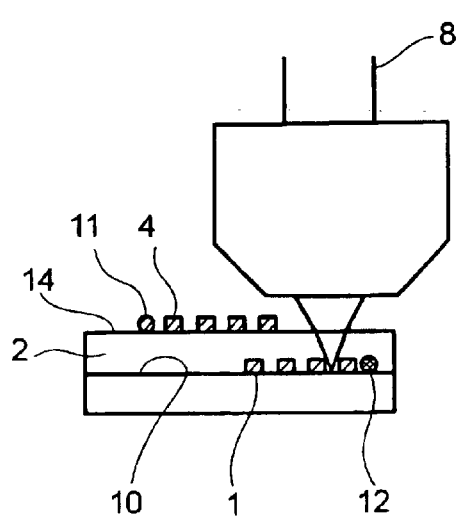
FIG. 12 is a drawing for the purpose of illustrating defect inspection according to the conventional technology and defect inspection according to a first embodiment of the present invention.
Figure 12:
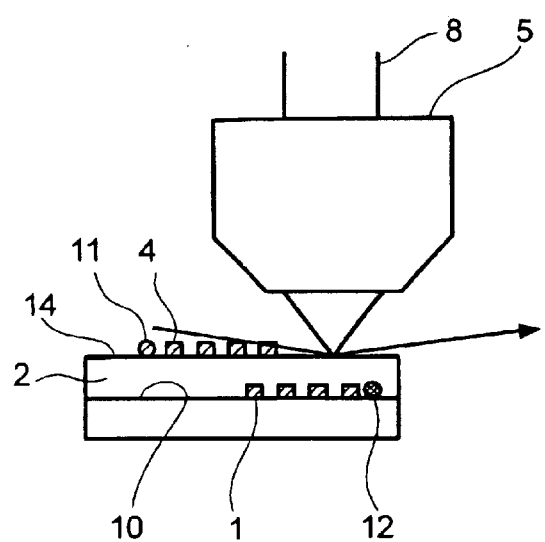
Figure 12:
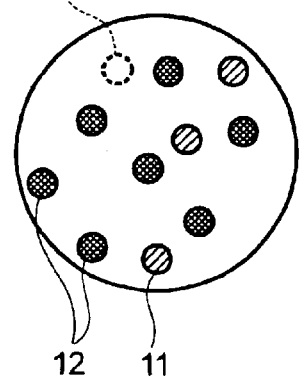
Figure 12:
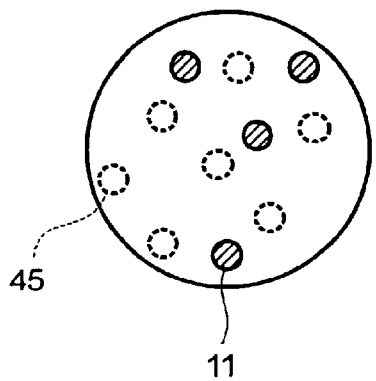

FIG. 12 schematically illustrates a comparison between inspection results from this embodiment, based on the above description, and inspection results from the conventional technology. For this embodiment, as shown in FIG. 12(b), an imaging optical system capable of imaging 0.15 micron widths (NA=0.85, λ=0.266 micron) is combined with an auto-focus optical system using S-polarized light with an illumination angle of at least 85 degrees. As a result, the fine circuit pattern 4 (0.15 micron width) on the surface 14 (height of the surface 14 within range of +/−0.2 micron) of the transparent film 2 can be imaged and the defect 11 can be detected with good sensitivity. Furthermore, overdetections 45 of the defects 12 in the lower layer of the transparent film 2 (with a thickness of at least 0.2 micron) are prevented.

Also, by using information about the thickness of the transparent film 2 stored in the external database 29d together with the Z-axis position information of the surface 14 of the transparent film 2 measured as described above, the Z-stage controller 13 can control the Z stage 22 so that the surface 10 of the lower layer of the transparent film 2 can be focused, thus allowing defects on the lower-layer surface 10 of the transparent film to be detected. In this manner, mode switching can be performed to detect defects on the surface 14 of the transparent film 2 or defects on the lower-layer surface 10.

Also, inspection can be performed on a wafer while performing this type of mode switching depending on position. Furthermore, information can be provided for both surfaces of the transparent film 2 by obtaining an image focused on the surface 14 of the transparent film 2 and an image focused on the lower-layer surface 10 for the same position.

In the conventional inspection conditions (S-polarized light at an illumination angle of less than 85 degrees (approximately 58 degrees)) shown in FIG. 12(a), the focus is on the lower-layer surface 10 of the transparent film 2. As a result, this example results in overdetection of the defects 12, which should not be detected, and a missed detection 46 of a defect that should be detected.

The present invention simplifies the process for determining inspection conditions and shortens the time required for this process. The procedure for determining inspection conditions is described below.

(1) The auto-focus offset is initialized via the input/output module (the value of this auto-focus offset offset will vary by an amount corresponding to the thickness of the transparent film 2 depending on whether the focus is set to the surface 14 of the transparent film 2 or the focus is set to the lower-layer surface 10 of the transparent film 2).

(2) A trial inspection is performed on a section of the wafer. The detection results are reviewed to see if there are defects or false detections.

(3) Step (2) is performed multiple times with vertical adjustments made to the initial value of the auto-focus offset. Based on this, the optimal conditions (most defects and least false detections) are determined. These conditions are recorded by the controller into a separate inspection conditions determination file, which is recorded in the external database via the network.

(4) The entire surface of the wafer is inspected. Representative positions are reviewed to confirm that there are no false detections.

The determined inspection conditions are stored in a file and saved by the controller into the external database via the network. The saved inspection conditions are read and used by other inspection apparatuses on the network. To provide quick implementation of this process for determining conditions, it is necessary for the optimal auto-focus offset to be determined quickly.

With inspection conditions that do not satisfy the main requirements of the present invention as shown in FIG. 12(a), the focus is on the upper layer in regions containing patterns on the upper layer and on the lower layer in regions that do not contain patterns on the upper layer. Thus, overdetection of defects 14 which should not be detected and missed detections 46 of defects that should be detected take place. As a result, the determination of an optimal auto-focus offset as described in (3) above is time-consuming.

In contrast, with the method using the present invention as shown in FIG. 12(b), the focus is always on the upper layer regardless of the presence of patterns on the upper layer. Thus, an offset based on the upper-layer surface can be easily determined. For this reason, the time required for determining conditions can be shortened.

The example above presents conditions for the present invention when the circuit pattern width is 0.15 microns. As circuit patterns become thinner in the future, the resolution Res from Equation (3) must be improved, and the wavelength λ of the illumination beam and the numerical NA of the object lens must be improved as well. This will result in a shallower depth of focus DOF in Equation (4), which will then require further reductions in the height detection error shown in FIG. 10(b). For S-polarized light, the illumination angle must be at least 88 degrees (value 43 in FIG. 10(b)), but this is possible using the architecture of the present invention.

Figure 13:
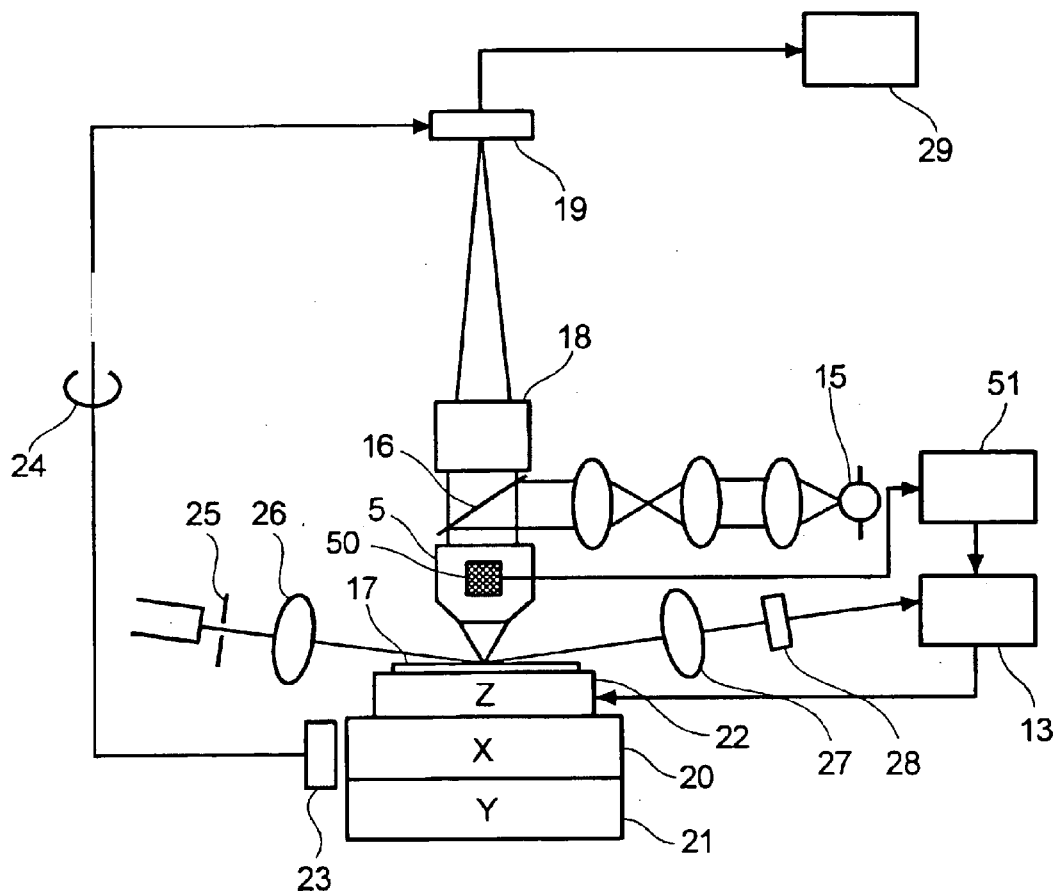
FIG. 13 is a drawing showing the architecture of a semiconductor wafer defect inspection apparatus according to a second embodiment of the present invention.

FIG. 13 shows the architecture of a defect inspection apparatus for semiconductor wafers according to a second embodiment of the present invention. The difference between this embodiment and the first embodiment described above is the addition to the first embodiment of a temperature sensor 50 and a focal position offset adjustment module 51.

In the objective lens of the defect inspection apparatus, aberration correction is provided for short illumination wavelengths and the lens is often formed from multiple lenses. Thus, even a temperature change of approximately 1 degree Celsius can lead to variations in the focal distance relative to the focal depth. Thus, in order to maintain the properties described with reference to the first embodiment over long periods of time, corrections must be applied to the focal distance, which can vary over time. Since the auto-focus optical system uses a different optical path from that of the imaging optical system, variations in the focal distance will lead to the height of the wafer 17 being adjusted to positions not aligned with the focal position, resulting in a defocused image.

Figure 14:
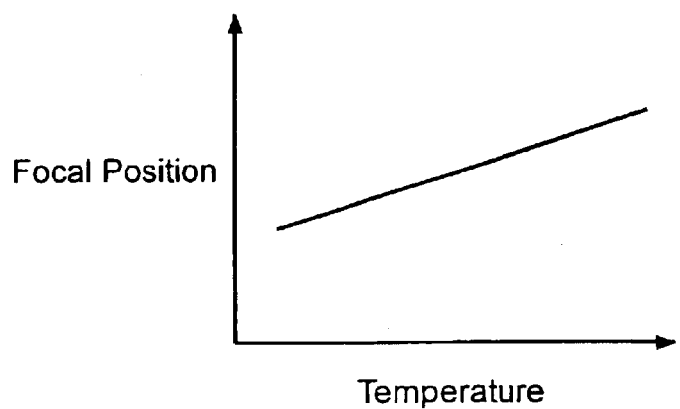
FIG. 14 is a drawing showing the relationship between temperature and depth of focus in an imaging optical system.

As temperature changes, lenses expand or contract, causing the focal distance to vary. Thus, the relationship between temperature and focal distance is measured beforehand. FIG. 14 shows an example of sample measurements. The horizontal axis indicates temperature and the vertical axis indicates focal distance. These can be measured ahead of time by varying the temperature. The relationship shown in FIG. 14 can also be calculated by using optical simulations.

If the relationship shown in FIG. 14 is known, the current focal distance can be predicted from the temperature of the objective lens 5 as measured by the temperature sensor 50. Thus, a correction can be applied to the focal position offset. To allow this, the relationship between temperature and focal position offset (the relationship shown in FIG. 14) is measured or calculated using simulations ahead of time and stored in the focal position offset adjustment module 51. Based on the temperature detected by the temperature sensor 50, the focal position offset adjustment module 51 predicts the focal position offset from the relationship shown in FIG. 14. Using this prediction value, a signal for correcting the focal position offset is sent to the Z stage controller 13. This allows focal position offsets resulting from temperature variations to be corrected by the focal position offset adjustment module 51. The focal position offset adjustment module 51 can be implemented, for example, so that the offset adjustment is added to the previous origin (zero point).

Figure 15:
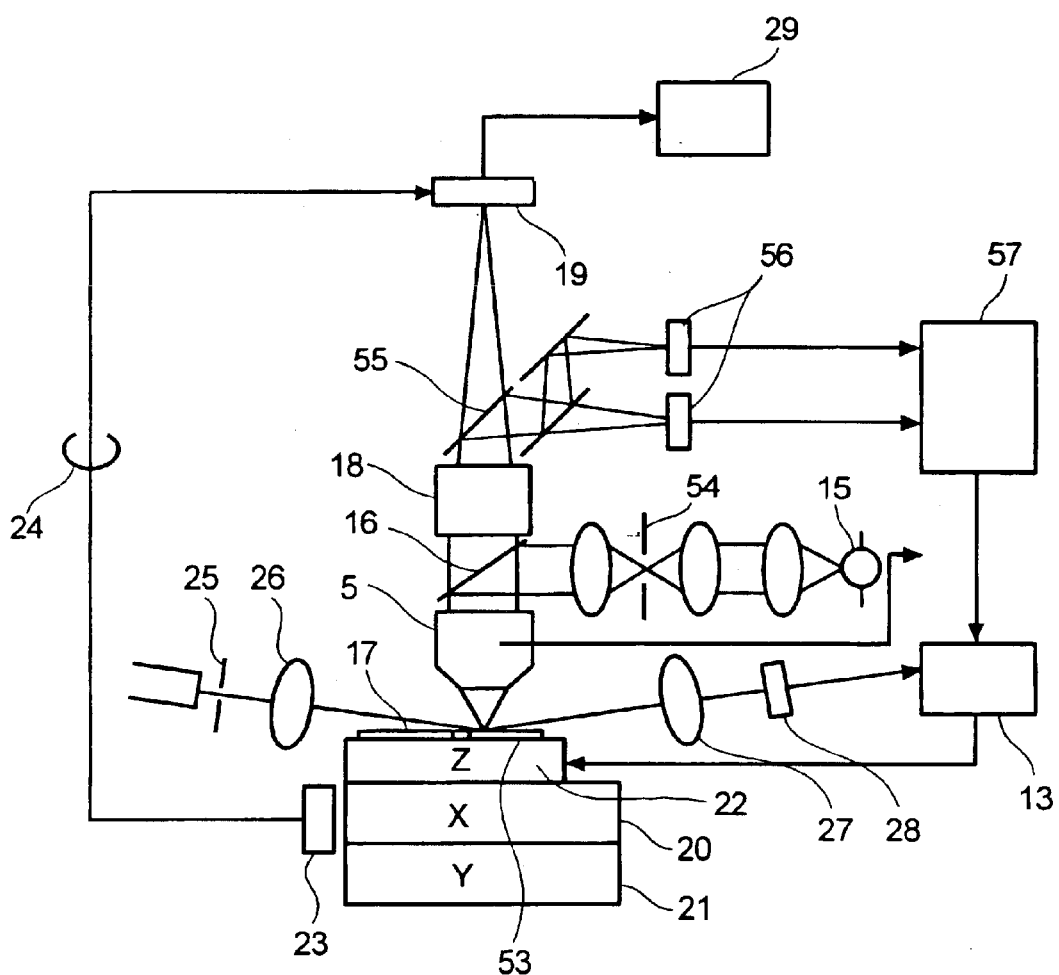
FIG. 15 is a drawing showing the architecture of a semiconductor wafer defect inspection apparatus according to a third embodiment of the present invention.

FIG. 15 shows the architecture of a defect inspection apparatus for semiconductor wafers according to a second embodiment of the present invention. The difference between this embodiment and the first embodiment described above is the addition to the first embodiment of a TTL focal position measurement optical system and a specimen 53 used by the focal position measurement optical system for focal position measurements. As in the second embodiment, this embodiment provides focal distance correction over time for the imaging optical system.

Figure 16:
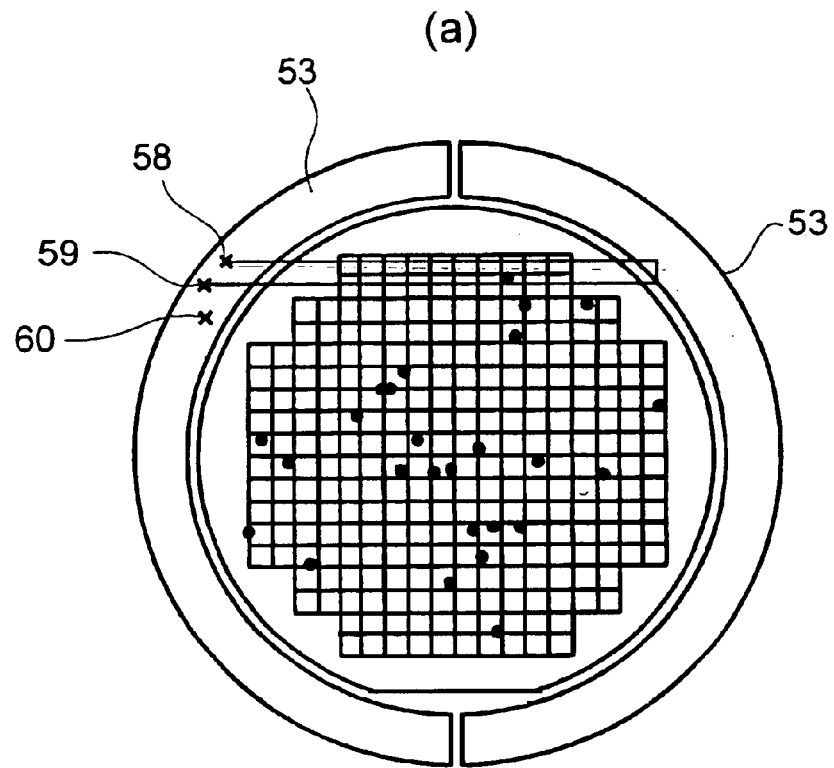
FIG. 16 is a drawing for the purpose of illustrating a focal position measurement specimen and stage moving sequences during inspections in a third embodiment of the present invention.
Figure 16:
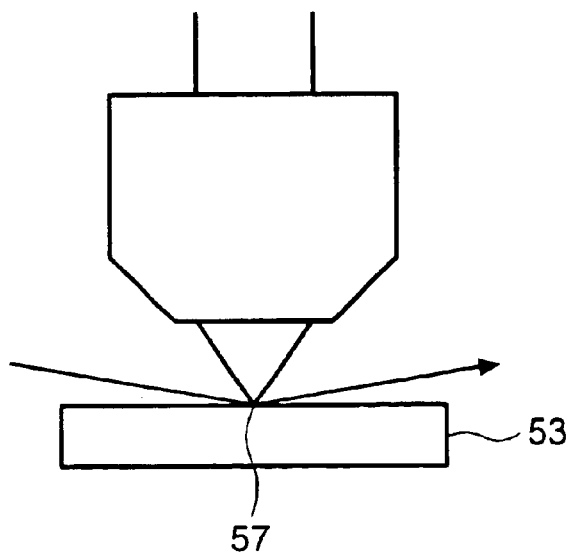

The focal position measurement specimen 53 is set up so that its surface height is roughly even with the height of the wafer 17. The flat surface of the specimen is formed as a mirrored surface that provides roughly total reflection of illumination. The specimen is attached along with the wafer 17 to the X, Y, Z stages (20, 21, 22). FIG. 16(a) shows a plan drawing indicating the relationship between the focal position measurement specimen 53 and the wafer 17. In this case, the specimen 53 is formed as a ring that surrounds the outer perimeter of the wafer 17. However, the shape of the specimen 53 is not restricted to this. The surface height of the specimen 53 can also be set to other values.

The TTL focal position measurement optical system is identical to a TTL auto-focus optical system. For example, an illumination light narrowed by a slit 54 disposed on the illumination optical path can be projected to a predetermined region on the specimen 53 (a region outside of the imaging illumination region, i.e., a region outside a region associated with the image sensor 19). The light reflected from the specimen 53 is split by a dichroic mirror 55. An optical path created by this split is further split in two using a half mirror and a mirror. Optical sensors 56 are disposed at a position roughly conjugate to the imaging position in the optical paths. The optical sensors 56 receive the two split beams and the output from these optical sensors 56 are compared by the TTL focal position measurement module 57 to measure the focus state. In this type of TTL focal position measurement optical system, the two sensors 56 will output identical contrasts when the surface height of the specimen 53 matches the focal position of the objective lens 5.

As a result, even if temperature variations or the like cause the focal position of the objective lens 5 to vary relative to the focal position due to the auto-focus optical system, the TTL focal position measurement system can measure a single position and an offset correction signal for the auto-focus point can be output from the TTL focal position measurement module 57 to the Z stage controller 13. This provides accurate correction of the auto-focal position offset. Since both the beam from the TTL focal position measurement optical system and the beam of the imaging optical system pass through the objective lens 5, the focal position of the TTL focal position measurement optical system can be treated as equivalent to the focal position of the imaging optical system. For this reason, the offset relative to the focal position due to the auto-focus optical system can be calculated accurately by the TTL focal position measurement module 57. By using the calculation results to send an offset correction signal for the auto-focal position from the TTL focal position measurement module 57 to the Z stage controller 13, the auto-focus offset can be accurately corrected. As a result, the reflection position 57 of the auto-focus optical system and the focal position 57 of the TTL focal position measurement system can be matched on the focal position measurement specimen 53. Consequently, the reflection position of the auto-focus optical system and the focal position of the TTL focal position measurement system (i.e., the focal position of the imaging optical system) can also be matched on the transparent film of the wafer 17.

Figure 17:
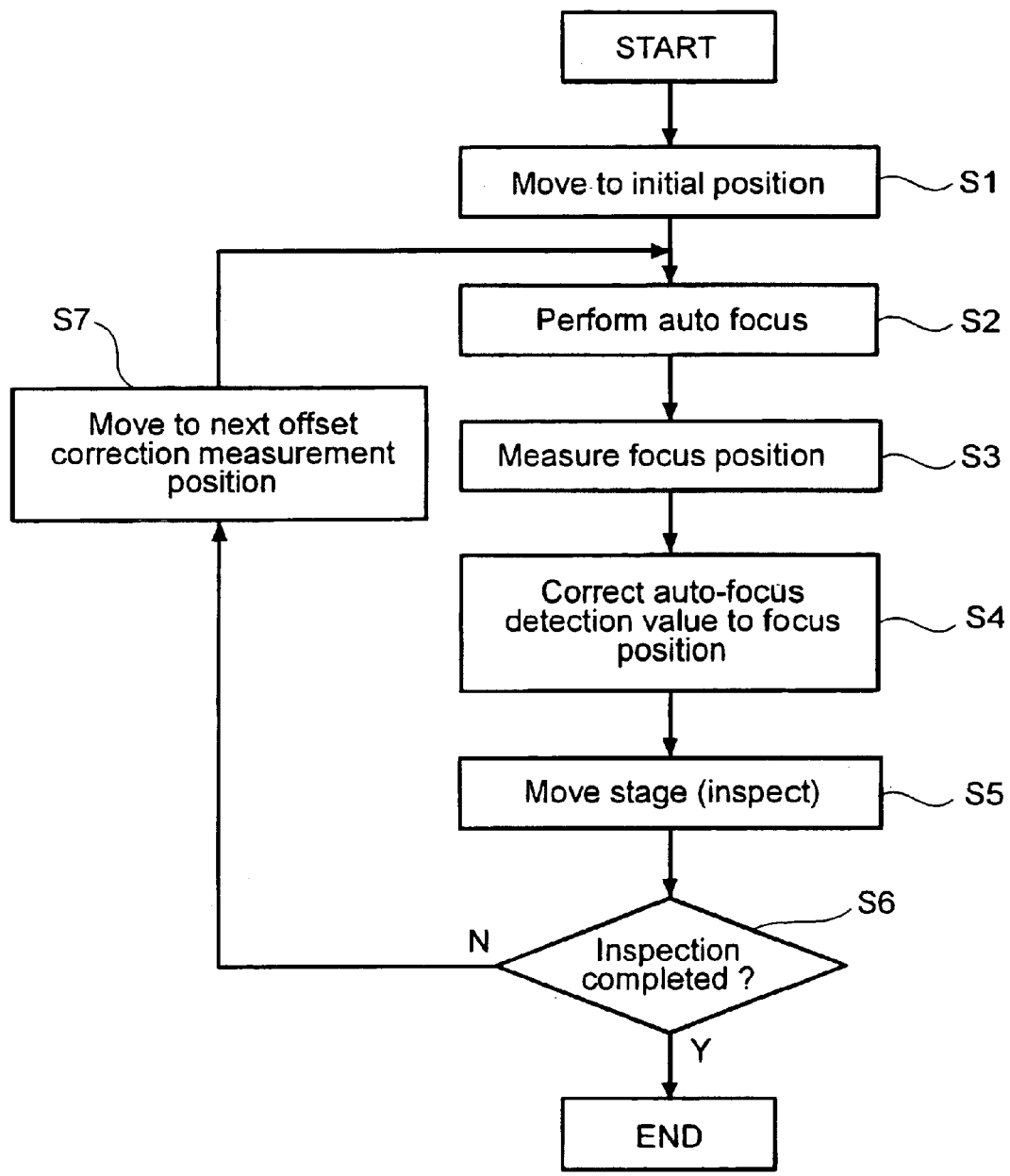
FIG. 17 is a flowchart showing an example of defect inspection operations in a third embodiment of the present invention.

The following is a description of the operations performed by this embodiment, with references to the flowchart shown in FIG. 17. First, when inspection is begun, the stages are moved so that an initial position 58 of the specimen 53 disposed around the wafer (see FIG. 16(a)) reaches the measurement position of the TTL focal position measurement optical system and the auto-focus optical system (step S1). Next, the measurement results from the auto-focus optical system for the initial position 58 of the specimen 53 are used to drive the Z stage 22 and provide auto-focusing (step S2). Then, the TTL focal position measurement optical system performs focal position measurement (step S3). Next, the offset between the focal position from the auto-focus optical system and the focal position from the TTL focal position measurement optical system is calculated by the TTL focal position measurement module 57. An auto-focal position offset correction signal based on this calculation is sent to the Z stage controller 13, and offset correction is applied so that the auto-focus detection value from the auto-focal position optical system matches the focal position of the objective lens 5 (step S4). Then, the X stage 22 is moved and defect inspection is performed for a predetermined region on the wafer 17. When the X stage 22 has been moved all the way across, the Y stage 21 is moved by one step, the X stage 22 is brought back, and defect inspection is performed for the next predetermined region on the wafer 17 (step S5). When the X stage 22 has been moved one cycle and the reflection position of the auto-focus optical system matches the position 59 on the specimen 53 (see FIG. 16(a)), the X stage 22 is temporarily halted and a determination is made as to whether defect inspection has been completed or not (step S6). If inspection has not been completed, the Y stage 21 is moved by one step, and the reflection position of the auto-focus optical system is moved to a subsequent offset correction measurement position 60 (see FIG. 16(*a*)). Then, at step S2 through step S4, the offset for the auto-focal position is corrected again and defect inspection is performed at step S5. These operations are repeated until the entire region of the wafer 17 has been inspected.

In the example described above, the auto-focal position offset correction is performed for each cycle of the X stage 22. The frequency at which to perform offset correction can, of course, be increased or decreased according to environmental factors and the like.

With the present invention as described above, fine patterns and defects on a transparent inter-layer insulative film can be detected with high sensitivity. Detection can be performed so that lower-layer patterns and defects on these layers are defocused, thus allowing only the defect from the process being inspected to be detected. As a result, defect counts can be accurately determined according to process. This allows effective fault prevention measurements to be implemented. Also, the present invention allows these features to be provided in a stable manner over long periods without being affected by environmental changes such as temperature variations.

The invention may be embodied in other specific forms without departing from the spirit or essential characteristics thereof. The present embodiment is therefor to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspection apparatus comprising:
a mount for mounting a specimen;
an illumination light to illuminate the specimen;
an imaging optical system forming an image of the specimen, the imaging optical system including an objective lens with a numerical aperture providing a resolution of at least 0.18 microns, when combined with the illumination light;
an opto-electrical converter positioned to detect the image of the specimen;
an auto-focus optical system including an illumination module and a detection module, the illumination module providing illumination on a surface of the specimen at an incident angle of at least 85 degrees relative to a normal of a surface of the specimen, the detecting module detecting light from the illumination module and reflected by the specimen;
an adjuster for adjusting a focal position of the imaging optical system based on a detection signal received from the auto-focus optical system;
a detector which detects defects on the specimen by processing electronic signals from the opto-electrical converter;
a temperature detector to measure temperature of the imagine optical system; and
a controller to control the adjuster using temperature information detected by the temperature detector.

2. Apparatus in claim 1 wherein the temperature detector measures a temperature at or near the objective lens of the imaging optical system.

3. Apparatus in claim 1 wherein the controller predicts a focal position offset based on temperature information detected by the temperature detector and a previously estimated relationship between temperature and focal position offset and uses the predicted focal position offset to control the adjuster based on the prediction.

4. A defect inspection apparatus comprising:
means for mounting a specimen;
means for illuminating the specimen;
an imaging optical system which forms an optical image of said illuminated specimen;
means for detecting an optical image of said specimen formed by said imaging optical system;
an auto-focus optical system obliquely illuminating a surface of said specimen and detecting light reflected from said specimen;
means for measuring temperature of said imaging optical system;
means for adjusting a focal position of said imaging optical system based on a detection signal from said auto-focus optical system and information about a temperature of said imaging optical system measured by said temperature measuring means;
means for detecting defects on said specimen by processing output from said means detecting an optical image; and
means for displaying, on a screen, information relating to defects of said specimen detected by said means for detecting defects.

5. A defect inspection apparatus as in claim 4 wherein said imaging optical system includes an objective lens with a numerical aperture providing a resolution of at least 0.18 microns, when combined with said illumination light from said illuminating means.

6. A defect inspection apparatus as in claim 4 wherein said auto-focus optical system provides illumination on a surface of said specimen mounted on said mounting means at an incident angle of at least 85 degrees relative to a normal of said specimen surface.

7. A defect inspection apparatus as recited in claim 4, wherein said means for adjusting adjusts a height of said specimen.

8. A defect inspection apparatus as recited in claim 4, wherein said means for illuminating illuminates a slit shape light on said specimen.

9. A method for inspecting defects comprising the following steps:
measuring a temperature of an imaging optical system;
illuminating a surface of a specimen at an angle relative to said surface;
detecting light reflected by said specimen;
determining, based on a signal obtained by detecting light reflected from said specimen, a focal position of said imaging optical system used to form an optical image of a surface of said substrate;
matching a height position of said specimen with said determined focal position;
illuminating said specimen at said matched height;
forming an optical image of said specimen using said imaging optical system equipped with an objective lens;
capturing an optical image of said specimen;
processing a signal obtained by capturing said optical image of said specimen and detecting defects of said specimen; and
wherein said step of determining a focal position is based on said temperature of said imaging optical system.

10. A method for inspecting defects on a specimen as in claim 9 wherein temperature at or near said objective lens of said imaging optical system is measured.

11. A method for inspecting defects on a specimen as in claim 9 wherein:
   a focal position offset is predicted based on temperature information detected by a temperature detecting means and a previously determined relationship between temperature and focal position offset; and
   a focal position of said imaging optical system is controlled based on said prediction.

12. A method for inspecting defects comprising the following steps:
   illuminating with a first light a surface of a specimen at an angle relative to said surface;
   measuring a temperature of an imaging optical system which has an objective lens;
   detecting light reflected from said surface of said specimen and determining, based on a signal obtained by said detecting and said measured temperature information, a focal position of an imaging optical system;
   adjusting a relative position between said specimen and said determined focal position;
   illuminating said specimen with a second light;
   forming an optical image of said specimen illuminated by said second light using said imaging optical system;
   capturing an optical image of said specimen; and
   processing a signal obtained by capturing said optical image of said specimen and detecting defects of said specimen.

13. A method for inspecting defects as in claim 12 wherein a temperature of said objective lens is measured in said step for measuring a temperature of said imaging optical system.

14. A method for inspecting defects as in claim 12 wherein said objective lens has a numerical aperture providing a resolution of at least 0.18 microns, when combined with said second light and said optical image is formed via said objective lens.

15. A method for inspecting defects as in claim 12 wherein said first light illuminating said surface of said specimen at an angle relative to said surface is illuminated with an incident angle of at least 85 degrees relative to a normal of said specimen surface.

16. A method for inspecting defects as recited in claim 12, wherein in said step of adjusting, a height of said specimen is adjusted.

17. A method for inspecting defects as recited in claim 12, wherein in said step of illuminating, a slit shape light illuminates said surface of said specimen.

* * * * *